United States Patent
Frisch

Patent Number: 5,788,842
Date of Patent: Aug. 4, 1998

[54] BIOMASS SEPARATION APPARATUS AND METHOD

[75] Inventor: Sam Frisch, Manalapan, N.J.

[73] Assignee: Envirogen, Inc., Lawrenceville, N.J.

[21] Appl. No.: 715,561

[22] Filed: Sep. 18, 1996

[51] Int. Cl.$^6$ ........................................... C02F 3/08
[52] U.S. Cl. .................... 210/618; 210/661; 210/792; 210/151; 210/189; 210/274
[58] Field of Search ........................ 210/617, 618, 210/661, 670, 675, 792, 150, 151, 189, 274

[56] References Cited

U.S. PATENT DOCUMENTS

| | | |
|---|---|---|
| 2,146,326 | 2/1939 | Bergius et al. |
| 3,705,082 | 12/1972 | Hondermarck et al. |
| 3,717,552 | 2/1973 | Hondermarch et al. |
| 3,855,120 | 12/1974 | Garbu ............... 210/618 |
| 3,910,826 | 10/1975 | Kataoka |
| 4,177,144 | 12/1979 | Hickey et al. |
| 4,250,033 | 2/1981 | Hickey et al. |
| 4,357,424 | 11/1982 | Bu'Lock |
| 4,545,909 | 10/1985 | Atkinson et al. ........ 210/618 |
| 4,561,974 | 12/1985 | Bernard et al. |
| 4,589,927 | 5/1986 | Allen et al. ............ 210/618 |
| 4,681,685 | 7/1987 | Sutton et al. |
| 4,707,252 | 11/1987 | Durot et al. ............ 210/151 |
| 4,708,936 | 11/1987 | Kulla et al. |
| 4,882,068 | 11/1989 | Blom |
| 4,892,818 | 1/1990 | Ramp |
| 4,904,600 | 2/1990 | Ramp |
| 4,954,259 | 9/1990 | Elmaleh et al. ......... 210/617 |
| 4,959,084 | 9/1990 | Wolverton et al. |
| 5,166,072 | 11/1992 | Krauling et al. |
| 5,173,194 | 12/1992 | Hering, Jr. |
| 5,260,216 | 11/1993 | Hirose et al. |
| 5,277,829 | 1/1994 | Ward ................... 210/189 |
| 5,316,945 | 5/1994 | Minuth |
| 5,342,781 | 8/1994 | Su |
| 5,487,829 | 1/1996 | Safferman et al. ...... 210/618 |
| 5,494,574 | 2/1996 | Unterman et al. |
| 5,573,663 | 11/1996 | Junius et al. ........... 210/189 |
| 5,573,671 | 11/1996 | Klein ................... 210/617 |

Primary Examiner—Peter A. Hruskoci
Assistant Examiner—Theodore M. Green
Attorney, Agent, or Firm—Miller & Christenbury

[57] ABSTRACT

A separator for use with a fluidized-bed bioreactor. A lift draws a slurry of liquid, media and biomass from the fluidized bed. A biomass discharge is connected to the lift and located above the height of the fluidized bed for discharging excess biomass. A media discharge, also connected to the lift, discharges media from the slurry and returns the media to the fluidized bed.

21 Claims, 4 Drawing Sheets

1

BIOMASS SEPARATION APPARATUS AND METHOD

FIELD OF THE INVENTION

The present invention relates to a fluidized-bed bioreactor, particularly to a bioreactor for separating contaminants from liquids and degrading the separated contaminants.

BACKGROUND OF THE INVENTION

It has become increasingly important in view of stricter environmental regulations to provide systems that effectively and efficiently remove and degrade contaminants from liquid waste. The development of fluidized-bed bioreactors has provided great benefits in this field.

However, many conventional fluidized-bed bioreactors suffer from operational drawbacks in that the media or carriers are subject to excessive buildup of biologically active materials (or "biomass"), thereby causing poor flow distribution, excessive media and/or biomass carryover, crusting, clogging and similar problems. The result is detrimental to system performance. Elimination of these drawbacks is a main object of this invention.

Attempts have been made in the past to overcome this long-standing problem. For example, U.S. Pat. Nos. 4,892,818 and 4,904,600, both issued to Floyd Ramp, describe a bioreactor. During a regeneration cycle, liquid feed into the bioreactor is increased to exceed the settling rate of packing particles so that the particles become dispersed. Liquid is delivered from the bioreactor to a separator, contaminants are removed from the liquid, and the liquid is recycled into the bioreactor through a pump. A retaining screen between the bioreactor and separator prevents particles from circulating through the separator.

U.S. Pat. No. 5,173,194, issued to Carl J. Hering, Jr., describes a filter bed wherein successive portions of filter media are removed for washing and subsequent return to the column. Lighthouse Separation Systems, Inc., of Fort Lauderdale, Fla., provides a similar system under the trademark VOLCANO with a so-called "backwash filter." Such systems are not adapted for biomass separation in fluidized-bed bioreactors.

Accordingly, there remains a need in the industry for an effective and efficient system for separating biomass that accumulates in a fluidized-bed bioreactor.

OBJECTS OF THE INVENTION

It is accordingly an object of the invention to provide an improved separator and method for use with fluidized-bed bioreactors.

It is another object of the invention to provide a system for separating excess biomass from a slurry of liquid, media and biomass.

Other objects and advantages of the invention will become apparent to those skilled in the art from the drawings, the detailed description of preferred embodiments and the appended claims.

SUMMARY OF THE INVENTION

One aspect of the invention provides a separator for use with a fluidized-bed bioreactor having a reaction chamber containing a slurry of liquid, media and biomass. A lift is provided to urge slurry to the separator from the fluidized bed. A biomass discharge is maintained above the height of the fluidized bed. The biomass discharge has a position that is preferably adjustable with respect to the reaction chamber. A media discharge is connected to the lift for return of media to the fluidized bed from the separator.

Slurry is preferably taken from an uppermost portion of the fluidized bed, and media is preferably returned to a location in the fluidized bed below the uppermost portion. A lift fluid such as gas is preferably used to urge a portion of slurry through the lift. The separator is preferably positioned outside the reaction chamber, but is alternatively positioned within the reaction chamber.

In operation, excess biomass is separated from a slurry of liquid, media and biomass by positioning a biomass discharge at a height above that of the fluidized bed. A portion of slurry is urged from the fluidized bed and into a lift so that excess biomass is discharged through the biomass discharge. Media from the slurry is discharged through a media discharge, and the media is subsequently returned to the fluidized bed. The height of the biomass discharge is preferably adjusted with respect to the reaction chamber in order to control the effectiveness of the separator.

DETAILED DESCRIPTION OF THE INVENTION

Figure 1:
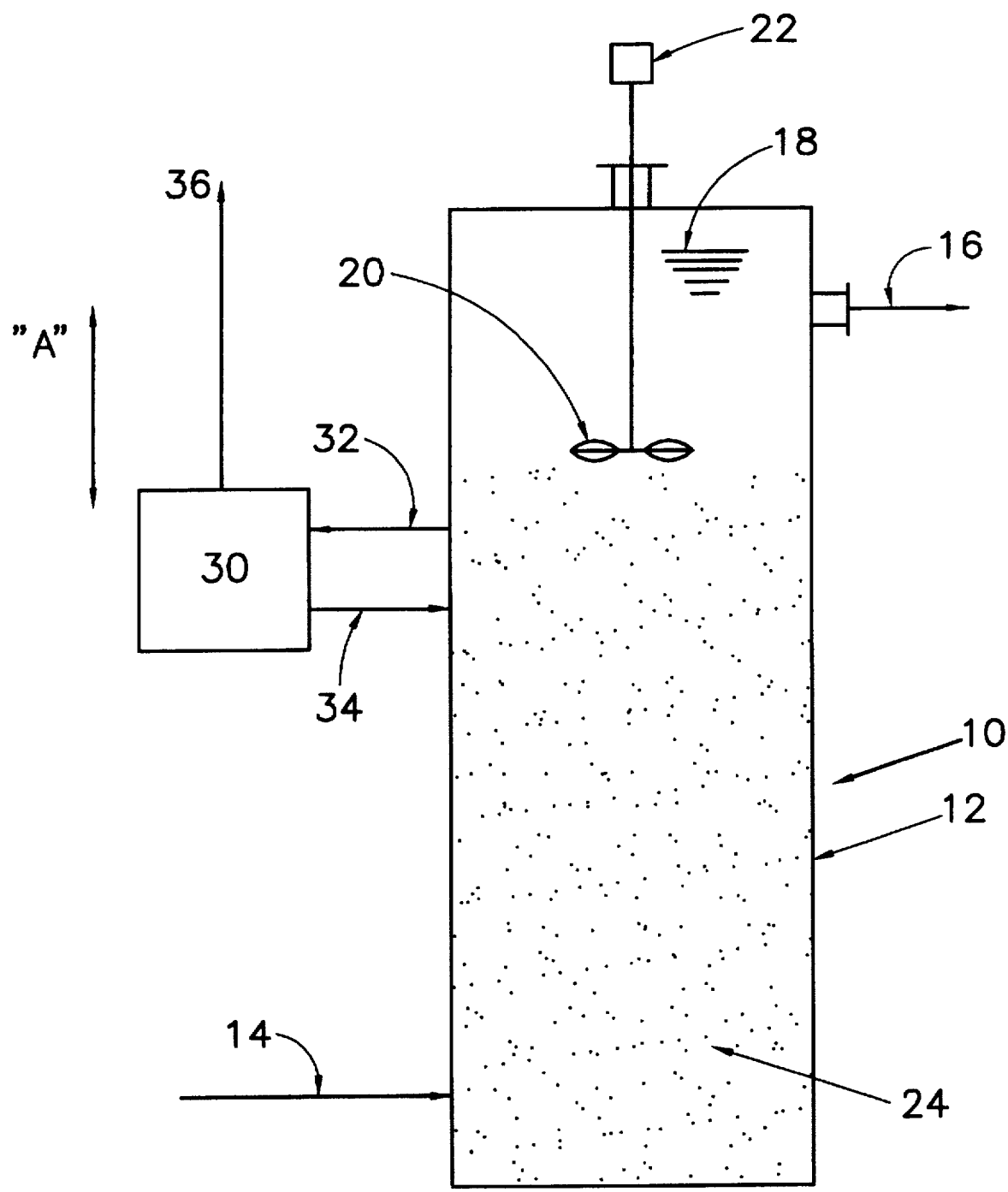
FIG. 1 is a schematic view of an embodiment of a fluidized-bed bioreactor having an external separator according to this invention.

It will be appreciated that the following description is intended to refer to specific aspects of the invention selected for illustration in the drawings and is not intended to define or limit the invention other than in the appended claims.

Figure 2:
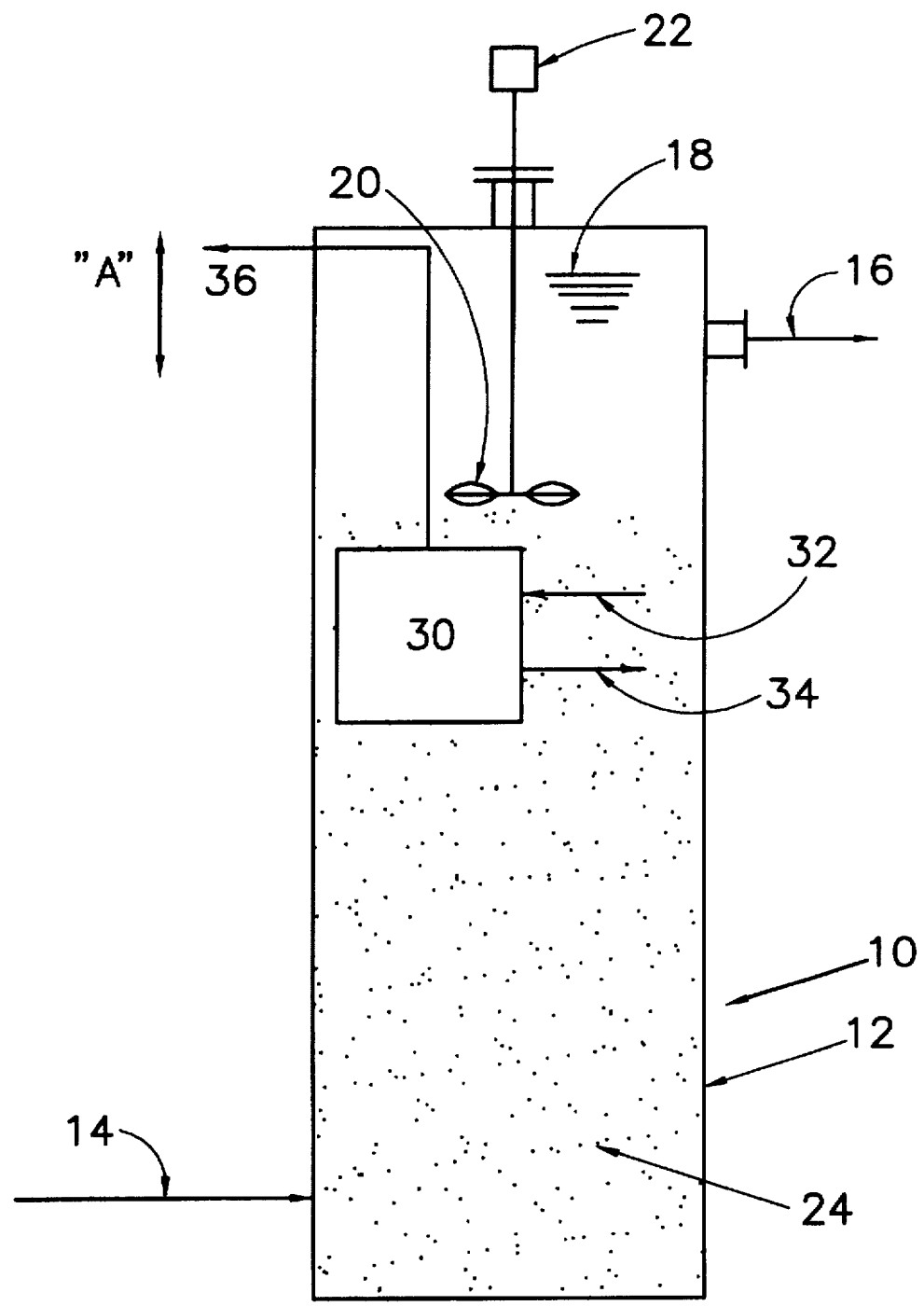
FIG. 2 is a schematic view of an embodiment of a fluidized-bed bioreactor having an internal separator according to this invention.
Figure 3:
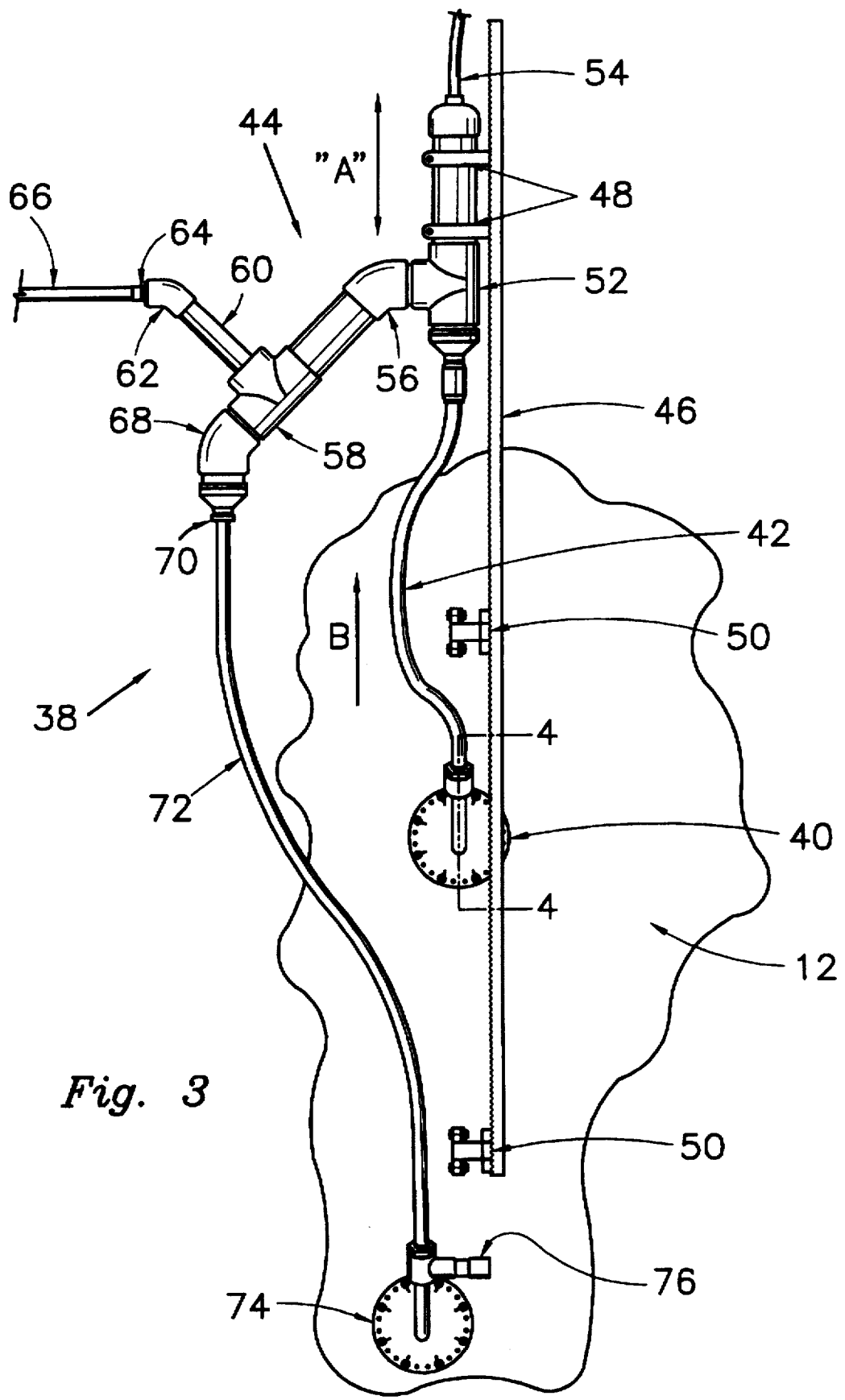
FIG. 3 is a side view of an embodiment of a separator according to this invention.
Figure 4:
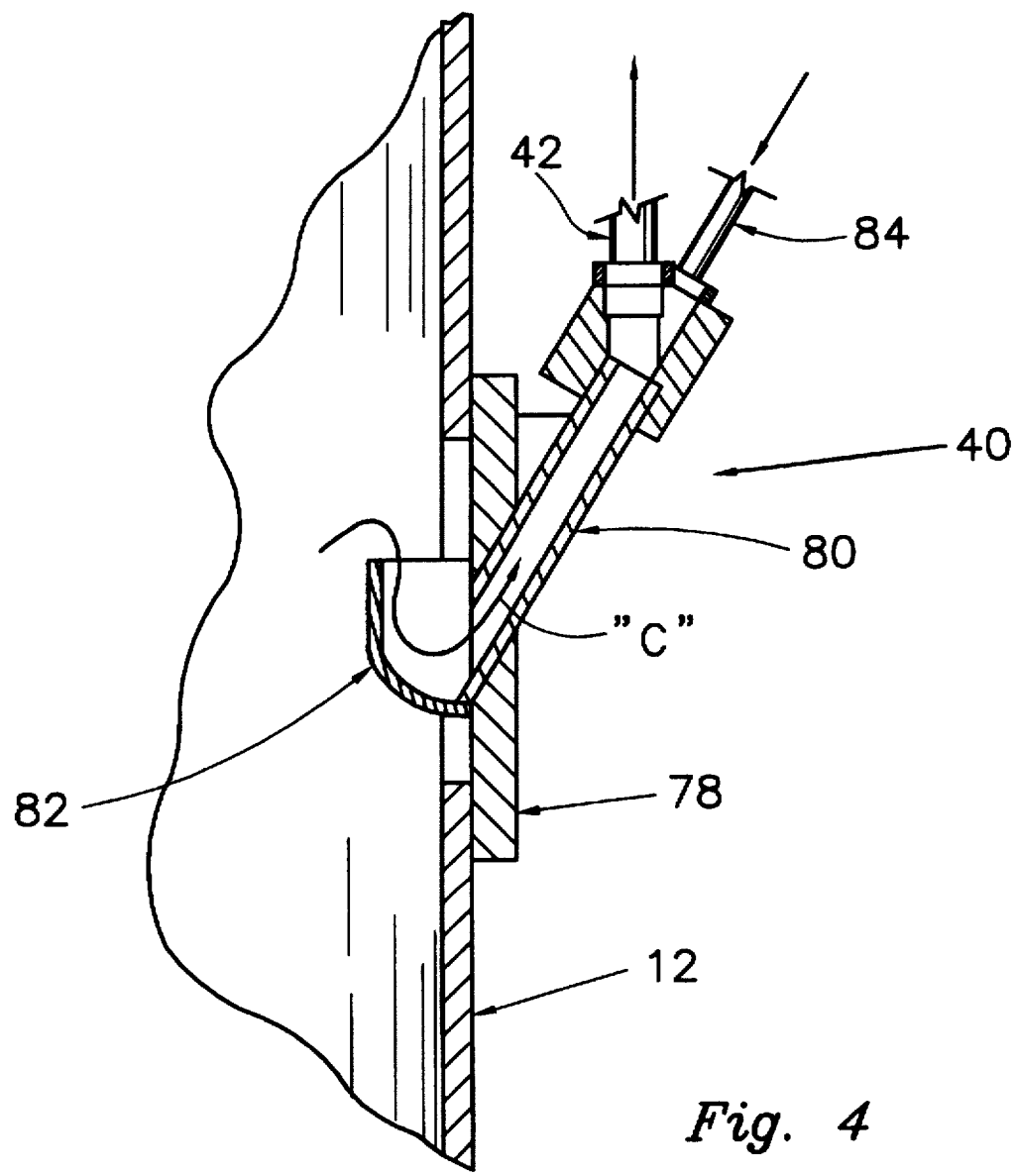
FIG. 4 is a cross-sectional side view of a detail of the separator embodiment shown in FIG. 3.

Turning now to the figures in general, several embodiments of a separator in accordance with aspects of the invention are shown for the purpose of illustration. FIGS. 1 and 2 illustrate embodiments of a bioreactor system according to this invention. FIG. 1 illustrates an example of an external separator and FIG. 2 illustrates an example of an internal separator. FIGS. 3 and 4 illustrate details of one possible embodiment of the system illustrated schematically in FIG. 1.

Referring specifically to FIGS. 1 and 2, the numeral "10" generally designates a fluidized-bed bioreactor adapted for degradation of contaminants in liquids. Bioreactor 10 includes a reaction chamber 12 adapted to contain a fluidized bed. An inlet 14 is provided for the introduction of sewage or other contaminated liquid to be treated in bioreactor 10. Representative contaminants include petroleum hydrocarbons, benzene/toluene/ethylbenzene/xylenes (BTEX) and trichloroethylene (TCE), although many other contaminants are contemplated, either alone or in combination.

An outlet 16 is provided for the removal of treated liquid or effluent. The liquid level in reaction chamber 12 is designated by level 18. An optional mixer or agitator 20 may be rotated by a motor 22 to agitate the fluidized bed and control the height of the fluidized bed. Such an agitator may be eliminated depending on the specific application. In fact, elimination of the agitator may be preferred. In any event, media and biomass are suspended in liquid within the fluidized bed.

The fluidized bed comprises a slurry 24 including liquid, a growth media or packing material (such as carbon granules, for example), and biomass. The media is supplied with microorganisms such as Pseudomonas, Actinomyces, or other bacteria, fungi or molds, for example, which can degrade contaminants carried by the liquid introduced through the inlet. Upon passing into contact with the microorganisms, contaminants are degraded. Degradation of the contaminant occurs by the usual mechanism of the particular microorganisms employed. As the quantity of biomass increases during the bioreaction process, it is desirable to remove some of the excess biomass. In most instances, excess biomass includes dead cell mass and residual nutrients and carrier fluid.

In order to remove excess biomass from slurry 24, a separator 30 is provided. As shown in FIG. 1, separator 30 is optionally positioned outside of reaction chamber 12. However, as shown in FIG. 2, separator 30 is alternatively positioned within reaction chamber 12, depending upon design choices and the specific application with which the bioreactor is used.

Whether separator 30 is positioned inside or outside the reaction chamber 12, a separator inlet 32 is provided for the flow of slurry 24 into separator 30 from the fluidized bed. Separator inlet 32 is optionally a lift, as will be described later. Also provided is a media return 34 through which media returns to the fluidized bed after passing through separator 30. Media return 34 is optionally a media discharge port, as will be described later. As shown in FIG. 2, separator inlet 32 and media return 34 are optionally positioned within reaction chamber 12. Alternatively, at least a portion of separator inlet 32 and at least a portion of media return 34 are positioned outside reaction chamber 12 (FIG. 1).

Separator 30 also includes a biomass discharge 36 through which excess biomass in slurry 24 is removed from the system. As shown in FIGS. 1 and 2, separator 30 and/or biomass discharge 36 is preferably adjustable in position or height in the direction generally designated "A". Such adjustment is preferred so that biomass discharge 36 can be positioned a desired distance above the liquid level 18 in reaction chamber 12. Such adjustment can also help to optimize the rate of biomass removal through discharge 36. It may also be beneficial by helping to maximize the amount of biomass removed, without removing an excessive amount of liquid and media through biomass discharge 36.

The preferred adjustability of separator 30 can be used by the operator of bioreactor 10, after it has been placed into operation, to adjust the separator and optimize its performance in response to any unique conditions at the site. This preferred feature also permits periodic adjustment of the system to compensate for variations in liquid level in reaction chamber 12 that may occur from changes in rate of liquid flow through reaction chamber 12 and any other variations known to occur in the field. Also, it is recognized that the flow rate of biomass through the discharge 36 is influenced by a combination of factors, including the rate of motive fluid flow, the height differential of the biomass discharge above the vessel liquid elevation, and the size of the biomass discharge opening and its resistance to flow. Most preferably, factors are adjusted to set biomass discharge rate so as to remove biomass from the system with a minimum amount of water and no media.

Referring to FIGS. 3 and 4, a particular embodiment of an external separator (such as the one illustrated schematically in FIG. 1, for example) is shown.

FIG. 3 shows an external separator assembly 38 that is connected to the outside of a reaction chamber such as reaction chamber 12. Separator assembly 38 includes a supply or lift assembly 40, details of which are provided in the cross-sectional view presented in FIG. 4.

Referring now to FIG. 4, assembly 40 is attached to the wall of a reaction chamber by means of a flange 78. Connected to flange 78 is an outlet line 80 and a baffle 82 through which slurry (such as slurry 24 shown in FIGS. 1 and 2) flows from within the reaction chamber in the direction designated "C". A motive fluid supply line 84 is provided for the introduction of motive fluid in the form of liquid or gas (such as air), although air is preferred.

Motive fluid introduced via supply line 84, when introduced in gaseous form, creates bubbles that urge the slurry in slugs upwardly through a lift line or passage 42 in the general direction labeled "B". When gaseous motive fluid is used, large bubbles of gas lift slurry in slugs and create a controlled turbulence to loosen biomass from the media. Motive fluid is introduced at a controlled rate and in a controlled frequency. Copending application Ser. No. 08/715,199, incorporated herein by reference, provides additional details of motive fluid introduction. Alternatively, motive fluid in liquid form urges the slurry upwardly under pressure. Passage 42 extends upwardly for connection to a separator body 44.

Separator body 44 is preferably attached to a channel 46 or similar structure in a manner that permits height adjustability in the direction "A". Separator body 44 is attached to channel 46 with clamps 48. In turn, channel 46 is attached to the reaction chamber with brackets 50. Accordingly, adjustment to the height of separator body 44 can be made by moving separator body 44 upwardly or downwardly along channel 46 and, when a desired height is established, fixing separator body 44 with respect to channel 46.

Components of separator body 44 will now be described. A tee 52 is provided to receive slurry from passage 42. Motive fluid (in a gaseous form) separates or disengages from the slurry in tee 52, and disengaged gas is discharged upwardly through a vent line 54. The slurry, which arrives in separator body 44 in slugs while the motive fluid is introduced, travels from tee 52, through an elbow 56, and arrives at a second tee 58. In the vicinity of tee 58, separation occurs between excess biomass in the slurry and media in the slurry. A pipe 60 preferably extends upwardly at an angle from tee 58 and terminates at an elbow 62 to which a biomass discharge opening 64 is connected.

Separation of biomass from liquid and media in the slurry is brought about at least in part by the difference in density between the biomass and media. Accordingly, biomass that is disengaged from the media will float upwardly to the biomass discharge.

As previously described, biomass discharge 64 is most preferably adjustable to a height that provides a desired biomass outflow rate by adjusting the height of the separator. Such adjustment is alternatively made by changing the length of pipe 60. Pipe 60 is preferably adjustable in length to alter the height of opening 64 with respect to the remaining components of the separator such as the media discharge described later. Additionally, the size of the opening provided in biomass discharge 64 is preferably selected so that a desired outlet flow velocity is achieved. For example, too great an output velocity from biomass discharge 64 may tend to draw an excessive amount of media and/or liquid out through discharge 64 along with the biomass. An appropriate velocity is most preferably achieved and maintained by adjusting the height of biomass discharge 64 with respect to the liquid level in the reaction chamber in conjunction with selection of an appropriate biomass discharge opening size. An excess biomass line 66 is connected to biomass discharge 64 for removal of excess biomass from the system for further processing, other uses or for destruction or disposal.

Downstream from tee 58 is provided an elbow 68 which terminates at a media discharge 70. Out through media discharge 70 flows media as well as the majority of liquid from the slurry (it is contemplated that some amount of liquid will be discharged through biomass discharge 64). A media return line 72 is connected to media discharge 70 in order to return media to the fluidized bed through a return assembly 74 that is mounted to the reaction chamber's wall. Media return line 72 is most preferably a clear, flexible hose to permit a system operator to monitor the flow of media back to the fluidized bed. A valve 76 is optionally provided to sample the returned media and/or to clear any pluggage that may occur in the media return line 72. Although media travels through line 72 largely under the influence of gravity, other means for assisting flow are contemplated.

The operation of a separator according to this invention will now be described with general reference to the figures. A motive fluid such as air is injected to urge a portion of slurry upwardly through a lift passage. Excess biomass is discharged through a biomass discharge that is maintained at a height above the height of liquid in the reaction chamber. Media from the slurry is discharged through a media discharge for return to the fluidized bed by means of a media return line.

Many modifications to the particular embodiments shown for illustration in the drawings can be made without departing from the spirit or the scope of this invention. For example, the separator assembly can be located within the reaction chamber or outside the reaction chamber.

If the separator assembly, or a portion thereof, is located within the reaction chamber as illustrated schematically in FIG. 2, the separator may be formed from concentric tubing or pipes which cooperate to define a lift passage for slurry, discharge openings for biomass and media, and a media return. Such a concentric assembly may take a wide variety of forms, depending upon design constraints. A concentric assembly is optionally used to form an external separator assembly as well, although an external assembly such as the one illustrated in FIGS. 3 and 4 is preferred. Also, although the biomass discharge is preferably positioned at a height greater than that of the liquid in the reaction chamber, the height of the biomass discharge is preferably adjustable upwardly or downwardly. Many additional modifications are contemplated.

In any embodiment or modification thereof, a separator according to this invention provides significant benefits. It permits the separation-out of biomass that can accumulate during continuous fluidized-bed bioreactions. Without removing biomass, the performance of the bioreaction system may become diminished. Accordingly, the separator and method according to this invention provide substantial improvements to the effectiveness of fluidized-bed bioreactors.

Although this invention has been described in connection with specific forms thereof, it will be appreciated that a wide array of equivalents may be substituted for the specific elements shown and described herein and that a wide array of equivalents may be substituted for the apparatus and structure described herein without departing from the spirit of this invention as it is defined in the appended claims.

What is claimed is:

1. A fluidized-bed bioreactor having a separator adapted to separate biomass from a slurry of liquid, media and biomass, said bioreactor comprising:

a reaction chamber constructed and arranged to contain a fluidized bed of said slurry, an inlet through which liquid to be treated enters said reaction chamber, and an outlet through which treated liquid exits said reaction chamber;

a separator body connected adjacent to said reaction chamber for receiving a portion of said slurry from said fluidized bed;

a lift connected adjacent to said separator body for flow of said slurry, said lift comprising a lift inlet for lift fluid, wherein said lift fluid is introduced into said lift through said lift inlet to urge said portion of said slurry through said lift towards said separator body;

a biomass discharge connected adjacent to said separator body for flow of biomass from said portion of said slurry urged through said lift; and a media discharge connected adjacent to said separator body for flow of media from said portion of said slurry urged through said lift, said media discharge defining a return passage connected to said reaction chamber for flow of said media from said media discharge and into said fluidized bed.

2. The bioreactor defined in claim 1, wherein said lift is connected for flow of slurry from an uppermost portion of said fluidized bed.

3. The bioreactor defined in claim 2, wherein said return passage defined by said media discharge is connected for flow of said media into said fluidized bed at a position below said uppermost portion of said fluidized bed.

4. The bioreactor defined in claim 1, wherein said lift inlet for lift fluid comprises a gas inlet for introducing motive gas, thereby producing gas bubbles to urge said portion of said slurry through said lift.

5. The bioreactor defined in claim 1, wherein said biomass discharge, said media discharge and at least a portion of said lift are positioned outside of said reaction chamber.

6. The bioreactor defined in claim 1, wherein said biomass discharge, said media discharge and at least a portion of said lift are positioned within an interior of said reaction chamber.

7. The bioreactor defined in claim 1, wherein said position of said biomass discharge is adjustable with respect to said reaction chamber.

8. A fluidized-bed bioreactor for removing contaminants from a liquid, said bioreactor comprising:

a reaction chamber adapted to contain a fluidized bed comprising a slurry of liquid, media and biomass, said reaction chamber including an inlet for liquid to be treated and an outlet for treated liquid; and a separator for removing biomass from said slurry, said separator comprising a lift connected for flow of said slurry into said lift from said fluidized bed and having a lift fluid inlet through which lift fluid is introduced to urge a portion of said slurry through said lift, said separator further comprising a biomass discharge connected to said lift for flow of biomass from said slurry urged through said lift, wherein means is provided for maintaining the height of said biomass discharge above the height of liquid in said reaction chamber, said separator further comprising a media discharge connected to said lift downstream from said biomass discharge for flow of media from said slurry urged through said lift and a return passage connected to said media discharge for flow of said media from said media discharge and into said fluidized bed.

9. The bioreactor defined in claim 8, wherein said lift is connected for flow of slurry from an uppermost portion of said fluidized bed.

10. The bioreactor defined in claim 9, wherein said return passage is connected for flow of media from said media discharge and into said fluidized bed at a position below said uppermost portion of said fluidized bed.

11. The bioreactor defined in claim 8, wherein said lift fluid inlet comprises a gas inlet for introducing into said lift a motive gas, thereby producing gas bubbles to urge a portion of said slurry through said lift.

12. The bioreactor defined in claim 8, wherein said biomass discharge, said media discharge and at least a portion of said lift are positioned outside of said reaction chamber.

13. The bioreactor defined in claim 8, wherein said biomass discharge, said media discharge and at least a portion of said lift are positioned within an interior of said reaction chamber.

14. The bioreactor defined in claim 8, wherein the height of said biomass discharge is adjustable with respect to said reaction chamber.

15. A method for separating excess biomass from a fluidized bed of a bioreactor comprising a reaction chamber for containing a slurry of liquid, media and biomass; a lift for the flow of slurry from said fluidized bed; a biomass discharge connected to said lift; a media discharge connected to said lift; and a return passage for flow of media to said fluidized bed from said media discharge, the steps comprising:

(a) positioning said biomass discharge at a height above the height of liquid in said reaction chamber;

(b) urging a portion of said slurry from said fluidized bed and through said lift;

(c) discharging biomass through said biomass discharge from said slurry urged through said lift;

(d) discharging media through said media discharge from said slurry urged through said lift; and (e) returning media discharged through said media discharge, under the influence of gravity, to said fluidized bed.

16. The method defined in claim 15, wherein said urging step comprises introducing into said lift a lift fluid.

17. The method defined in claim 16, wherein said urging step further comprises introducing into said lift a gas and producing gas bubbles to urge a portion of said slurry upwardly through said lift.

18. The method defined in claim 15, wherein said urging step comprises urging a portion of said slurry from an uppermost portion of said fluidized bed.

19. The method defined in claim 18, wherein said returning step comprises returning media discharged through said media discharge to said fluidized bed at a position below said uppermost portion of said fluidized bed.

20. The method defined in claim 15, further comprising the step of adjusting said height of said biomass discharge with respect to said reaction chamber to control the rate of biomass flow through said biomass discharge.

21. A method for separating excess biomass from a fluidized bed of a bioreactor comprising an inlet through which liquid to be treated enters said bioreactor; an outlet through which treated liquid exits said bioreactor; a reaction chamber for containing a slurry of liquid, media and biomass; a separator body connected to said reaction chamber for receiving a portion of said slurry; a lift connected adjacent to said separator body for the flow of slurry; a biomass discharge connected adjacent to said separator body; a media discharge connected adjacent to said separator body; and a return passage for flow of media to said fluidized bed from said media discharge, the steps comprising:

(a) urging a portion of said slurry from said fluidized bed through said lift towards said separator body;

(b) discharging biomass through said biomass discharge from said slurry urged through said lift;

(c) discharging media through said media discharge from said slurry urged through said lift; and (d) returning media discharged through said media discharge, under the influence of gravity, through said return passage and into said fluidized bed.

* * * * *